United States Patent [19]

Lee

[11] 4,313,079
[45] Jan. 26, 1982

[54] BATTERY DEPLETION MONITOR

[75] Inventor: Yan S. Lee, Plymouth, Minn.

[73] Assignee: Medtronic, Inc., Minneapolis, Minn.

[21] Appl. No.: 112,592

[22] Filed: Jan. 16, 1980

[51] Int. Cl.³ .................. H02J 7/10; H03K 3/26
[52] U.S. Cl. ............................. 320/48; 307/304; 340/636
[58] Field of Search ............ 320/43, 48; 340/636; 307/304, 303; 324/433

[56] References Cited
U.S. PATENT DOCUMENTS 4,119,904 10/1978 Haglund ................... 320/48
4,217,535 8/1980 Suzuki et al. ............. 320/48

Primary Examiner—Robert J. Hickey
Attorney, Agent, or Firm—Robert C. Beck; Lew Schwartz; Joseph F. Breimayer

[57] ABSTRACT

A CMOS inverter is used to compare pacemaker battery voltage to a referenced voltage. When the reference voltage exceeds the measured battery voltage, the inverter changes state to indicate battery depletion.

3 Claims, 2 Drawing Figures

BATTERY DEPLETION MONITOR

BACKGROUND OF THE INVENTION

1. Field of the Invention

This invention relates to a circuit for monitoring battery voltage in an implanted cardiac pacemaker, and for indicating when a preselected battery depletion level is exceeded.

2. Description of the Prior Art

Typically, the useful service life of an implantable cardiac pacemaker is limited by the depletion characteristics of the battery power source which powers the pacemaker. As the battery depletes the output voltage decreases and the internal impedance of the battery increases. The increased impedance limits the amount of current which can be drawn from the battery by the pacemaker. Eventually the pacemaker will cease functioning because of inadequate battery voltage or insufficient current. It is desirable to provide a warning indication to notify the patient and his physician that the end of the useful service life of the pacemaker is being approached so that the failing pacemaker may be replaced before it ceases functioning.

In many prior art pacemakers the asynchronous pulse rate progressively decreases as the battery depletes. This reduction in pulse rate is used as the depletion indicator. Elective replacement of a pacemaker would typically take place when the measured asynchronous pulse rate has decreased by ten percent. However, recently introduced digital pacemakers, which are crystal controlled, do not undergo a progressive change in pulse rate as the battery depletes. As a consequence, additional circuitry must be added to these pacemakers to initiate an end-of-life indicator.

SUMMARY OF THE INVENTION

In the invention a first reference voltage derived from the pacemaker battery voltage is supplied to the drain of the p-channel device of a CMOS inverter. A second voltage derived through a resistor chain from the battery voltage is supplied to the gate input of the inverter. This second voltage is a measured voltage proportional to the battery voltage. The inverter compares the two voltages, and it will change state as the second measured voltage approaches the reference voltage.

The advantages and characterizing features of the present invention will become apparent upon reading the detailed description of the preferred embodiment in conjunction with the drawing.

DETAILED DESCRIPTION OF THE PREFERRED EMBODIMENT

Figure 1:
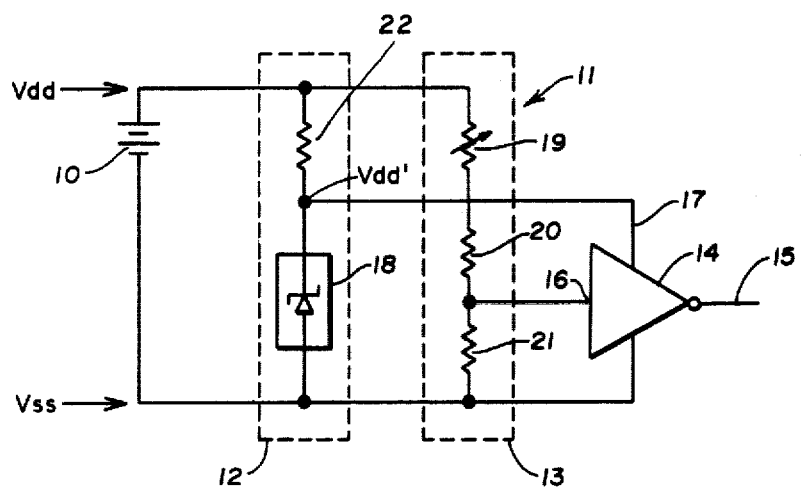
FIG. 1 is a schematic diagram of a single level embodiment of the present invention; and, FIG. 2 is a schematic diagram of the multiple level embodiment of the battery depletion indicator.

In FIG. 1 the power source 10 is shown connected to the battery depletion monitor circuit 11 which comprises a voltage reference circuit 12 and voltage measuring circuit 13. These voltages are compared by inverter 14 which responds by toggling its output 15 when the voltage supplied to the input gate 16 of the inverter is less than the device threshold set by the voltage supplied to the drain of the p-channel device 17 by the voltage reference circuit 12.

The voltages represented in the circuit are measured between the anode and cathode of the battery and are labeled Vdd and Vss respectively. The voltage regulator device 18 which may be a zener diode will suppply a stable reference voltage of a magnitude of less than the potential difference between Vdd and Vss to the drain connection of inverter 14. As shown in the figure, the drain connection 17 voltage is constant throughout the service life of the battery. The voltage divider formed by resistors 19, 20 and 21 in measuring circuit 13 generate a gate voltage at input 16 which is directly proportional to the supply voltage of the battery 10 and which varies over the life of the battery.

It is the property of a CMOS inverter to change state when the gate voltage present at gate 16 is approximately one-half the potential between the drain and source connections of the inverter. Therefore, early in the operating life of the device the voltage at input gate 16 supplied by the measuring circuit 13 exceeds the threshold voltage of inverter 14. As the battery depletes the potential at input gate 16 of the inverter 14 approaches one-half value of the drain voltage. When this threshold is reached, the output of the inverter 15 will switch from the low to the high state. The signal available at output 15 when properly conditioned will initiate the end-of-life indicator of the pacemaker.

The power consumption of the circuit shown in FIG. 1 is very low. The inverter 14 draws current only during the state transition which is initiated by the threshold voltage at gate 16. In the quiescent condition this inverter's current drain will be its leakage current which is negligible. The primary current drain of the circuit of FIG. 1 is due to network 12 and network 13. However, due to the high impedance of the inverter 14, the values for the resistors 19, 20, 21 and 22 may be quite large, limiting their current drain to a minimum.

Figure 2:
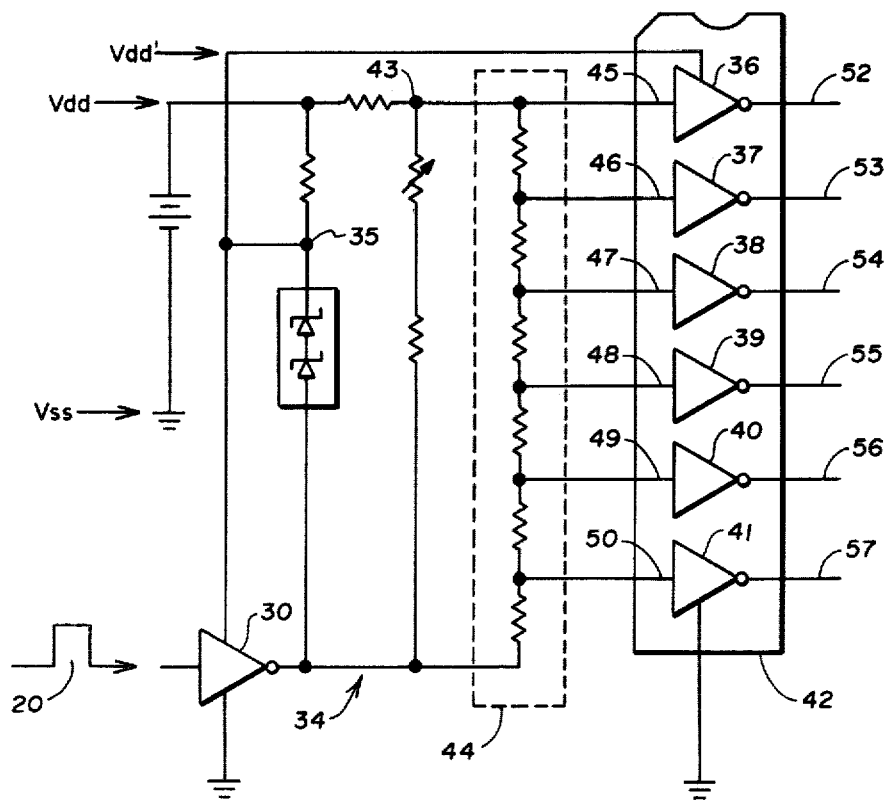

In the FIG. 2 embodiment current consumption is further minimized by strobing the battery depletion indicator periodically for a short period of time. When operating in a pacemaker, the strobe pulse 20 may be generated by the pacemaker output circuitry at a repetition rate equal to the pulse rate of the pacemaker, and at a time just prior to the initiation of the output pulse.

The strobe pulse is buffered by an inverter 30. When the strobe pulse goes high, the n-channel transistor of the inverter 30 enters a low impedance state permitting current to be sourced to the depletion indicator 34.

In this embodiment the reference voltage at node 35 is supplied to the drain connections of the inverters 36–41 in array 42. The measured voltage proportional to battery depletion is present at node 43. This voltage is divided down be a resistor network 44. Taps 45–50 of this network supply the ratioed voltage to the individual input gates of the inverter array 42. Consequently, progressively reduced fractions of the measured battery voltage are applied to the gates of inverters 36–41. The output states of these inverters at outputs 52–57 are determined by gate voltages applied to individual gates and the value of the reference voltage applied to the drain connection 51 of the array 42.

In operation the outputs 52–57 will sequentially change state as the battery depletes until the reference voltage is reached. At the reference voltage, outputs of all inverters will be in the high state indicating depletion to the reference voltage level.

The accuracy of this depletion monitor is set by the potentiometric resistor network 44. The resolution of the monitor is determined by the number of taps on the resistor network.

When used as a depletion indicator for an implantable pacemaker, the outputs 52-57 can be utilized to digitally select appropriate pulse width stretching to noninvasively indicate battery voltage.

Having thus described the invention it will be apparent that changes and modifications may be made without departing from the spirit and scope of the invention.

I claim:

1. A battery voltage monitor for sensing and indicating battery depletion in a pacemaker comprising at least one CMOS inverter having drain, source, input gate and output connections;

said source connection connected to ground potential;

said drain connection connected to a reference voltage;

said reference voltage source producing a reference voltage lower than the undepleted battery voltage;

a voltage divider connected to said battery for providing a measured voltage indicative of battery depletion to said input gate, such that said measured voltage level exceeds said reference voltage level in the undepleted battery condition; and wherein the voltage at said output connection changes from a low state to a high state to indicate the attainment of a preset depletion level when said measured voltage reaches a level substantially equal to one-half of said reference voltage.

2. A battery voltage monitor for sensing and indicating battery depletion in a pacemaker comprising:

a plurality of CMOS inverters having drain and source connections connected in parallel, respectively, a plurality of independent input gates and output connections;

said source connections connected to ground potential;

a reference voltage source producing a reference voltage level below the undepleted battery voltage level, connection to drain connections;

a voltage network having a plurality of taps respectively connected to said input gates for delivery to said gates measured voltages indicative of the level of battery depletion; and a plurality of output connections whose output state changes to indicate when the respective input gate voltages are substantially equal to one-half of said reference voltage.

3. The monitor of claim 2 further including strobe means for periodically connecting said source connections to ground potential.

* * * * *